(12) United States Patent
Burke et al.

(10) Patent No.: US 12,376,955 B2
(45) Date of Patent: Aug. 5, 2025

(54) ENDOPROSTHESIS WITH STRESS REDUCING FEATURES

(71) Applicant: BOSTON SCIENTIFIC SCIMED, INC., Maple Grove, MN (US)

(72) Inventors: Martin Burke, Galway (IE); Daniel Tuck, Galway (IE); Molly Solomon, Lowell, MA (US); Robert Sears, Maple Grove, MN (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 638 days.

(21) Appl. No.: 17/697,551

(22) Filed: Mar. 17, 2022

(65) Prior Publication Data

US 2022/0304795 A1    Sep. 29, 2022

Related U.S. Application Data

(60) Provisional application No. 63/164,766, filed on Mar. 23, 2021.

(51) Int. Cl.
*A61F 2/04* (2013.01)
*A61F 2/90* (2013.01)

(52) U.S. Cl.
CPC .............. *A61F 2/04* (2013.01); *A61F 2/90* (2013.01); *A61F 2002/046* (2013.01);
(Continued)

(58) Field of Classification Search
CPC ........ A61F 2/04; A61F 2/90; A61F 2002/046; A61F 2210/0014; A61F 2250/001;
(Continued)

(56) References Cited

U.S. PATENT DOCUMENTS 5,007,926 A    4/1991  Derbyshire
5,258,027 A    11/1993 Berghaus
(Continued)

FOREIGN PATENT DOCUMENTS

EP    2698126 A1    2/2014
WO    02055125 A2   7/2002

OTHER PUBLICATIONS

International Search Report for International Application No. PCT/US2015/033268 dated Aug. 14, 2015.
(Continued)

*Primary Examiner* — Jerrah Edwards
*Assistant Examiner* — Hanna L Pasqualini
(74) *Attorney, Agent, or Firm* — Seager, Tufte & Wickhem, LLP

(57) ABSTRACT

An endoprosthesis configured to shift between a collapsed configuration and an expanded configuration may include a tubular scaffold formed from a single filament knitted about a central longitudinal axis and defining a length from a proximal end to a distal end, the tubular scaffold including a plurality of rows of loops and a plurality of rows of rungs arranged around the central longitudinal axis in an alternating fashion; and a polymeric covering extending along the tubular scaffold. Each row of loops and each row of rungs extends longitudinally along the tubular scaffold between the proximal end and the distal end. The tubular scaffold includes a first cutout region extending along a majority of the length of the tubular scaffold and a second cutout region extending along a majority of the length of the tubular scaffold. The polymeric covering is uninterrupted along the first cutout region and the second cutout region.

14 Claims, 12 Drawing Sheets

(52) U.S. Cl.
CPC . *A61F 2210/0014* (2013.01); *A61F 2250/001* (2013.01); *A61F 2250/0073* (2013.01)

(58) Field of Classification Search
CPC ................ A61F 2250/0073; A61F 2/07; A61F 2002/043; A61F 2/06; A61F 2002/061; A61F 2002/072; A61F 2002/075; A61F 2002/077; A61F 2/82; A61F 2002/823; A61F 2002/828; A61F 2/856; A61F 2/86
See application file for complete search history.

(56) References Cited

U.S. PATENT DOCUMENTS

| | | | |
|---|---|---|---|
| 5,366,504 A | 11/1994 | Andersen et al. | |
| 5,383,926 A | 1/1995 | Lock et al. | |
| 5,480,431 A | 1/1996 | Freitag et al. | |
| 5,824,038 A | 10/1998 | Wall | |
| 5,928,261 A | 7/1999 | Ruiz | |
| 6,551,352 B2 | 4/2003 | Clerc et al. | |
| 7,371,257 B2 | 5/2008 | Sahatjian et al. | |
| 7,513,907 B2 | 4/2009 | Lau et al. | |
| 7,647,931 B2 | 1/2010 | Pflueger et al. | |
| 7,955,374 B2 | 6/2011 | Erickson et al. | |
| 8,578,938 B2 | 11/2013 | Pflueger et al. | |
| 8,603,157 B2 | 12/2013 | Seguin et al. | |
| 9,918,585 B2 | 3/2018 | Ye et al. | |
| 10,864,069 B2 | 12/2020 | Seddon et al. | |
| 2003/0024534 A1 | 2/2003 | Silvestri et al. | |
| 2003/0149488 A1 | 8/2003 | Metzger et al. | |
| 2004/0015225 A1 | 1/2004 | Kim et al. | |
| 2004/0215327 A1 | 10/2004 | Doig et al. | |
| 2008/0065209 A1 | 3/2008 | Pflueger | |
| 2010/0010620 A1 | 1/2010 | Weber | |
| 2010/0262216 A1 | 10/2010 | Xue | |
| 2014/0052231 A1 | 2/2014 | Lee | |
| 2015/0216653 A1* | 8/2015 | Freudenthal | A61F 2/2409 623/2.17 |
| 2017/0290653 A1* | 10/2017 | Folan | A61F 2/90 |
| 2019/0307586 A1 | 10/2019 | Gilmartin et al. | |

OTHER PUBLICATIONS

International Search Report and Written Opinion dated Jun. 14, 2022 for International Application No. PCT/US2022/020773.

* cited by examiner

ENDOPROSTHESIS WITH STRESS REDUCING FEATURES

CROSS REFERENCE TO RELATED APPLICATIONS

This application claims the benefit of and priority to U.S. Provisional Patent Application Ser. No. 63/164,766 filed on Mar. 23, 2021, the disclosure of which is incorporated herein by reference.

TECHNICAL FIELD

The present disclosure pertains to medical devices, and methods for manufacturing and/or using medical devices. More particularly, the present disclosure pertains to an improved design for an endoprosthesis or stent.

BACKGROUND

In general, the human body includes various lumens, such as a trachea, blood vessels, urinary, biliary, esophageal, or renal tracts, etc. These lumens sometimes become occluded or weakened, or otherwise in need of structural support. For example, the body lumen can be constricted by a tumor, occluded by plaque or a stricture, or weakened by an aneurysm. Endoprostheses or stents have been developed that may be implanted in a passageway or lumen in the body. In general, such endoprostheses are tubular members with a circular cross-section, examples of which include stents, stent grafts, covered stents, etc.

Current braided or knitted self-expanding endoprostheses may express a large degree of longitudinal flexibility due to design and device length. This may be advantageous for the purpose of device delivery, especially in more tortuous anatomical regions and for reduction in lumen straightening post-delivery, which is typically seen as being less traumatic on target lumens. In some cases, a bare endoprosthesis may include an additional coating where benign strictures are to be treated, stent removal may be a requirement, and/or where the coating is used to isolate a treated lumen from nutritional impaction (e.g., post bariatric surgery leak treatment, fistula treatment, etc.). Braided and knitted stents are sometimes used in the tracheobronchial lumens to help keep the airway open.

An issue with braided and knitted stents in the tracheobronchial lumens is the possibility of fracture and/or failure as a result of fatigue. Forced inspiration/expiration and/or coughing may lead to large deformation of the body lumen and corresponding deformation of a stent disposed in the body lumen. Due to the anatomy of the trachea and bronchi, the deformations of these lumens may be radially non-uniform and result in concentrated areas of high stress on the implanted stent. In the trachea, during forced inspiration/expiration and/or coughing the cartilage rings compress radially and the smooth muscle tissue indents. Sharp fold lines are formed resulting in a crescent shape. The implanted stent will deform in a similar manner causing areas of high stress and eventually possible stent fractures along the sharp fold lines. The bronchi undergo a more complete radial compression because the smooth muscle tissue and cartilage rings are more evenly distributed around the lumen, however there can still be stress concentrations in areas around the stent.

In isolation, these movements may be generally unharmful to the stent. However, repeated exposure to significant amounts of deformation may cause fatigue and/or fractures in the filament(s) that form the stent over time. In some cases, the fatigue and/or fracture may further cause a loss of covering integrity. There is an ongoing need to provide alternative endoprostheses or stents as well as alternative methods for manufacturing and using endoprostheses or stents.

SUMMARY

In one example, an endoprosthesis configured to shift between a collapsed configuration and an expanded configuration may comprise a tubular scaffold formed from a single filament knitted about a central longitudinal axis and defining a length from a proximal end to a distal end, the tubular scaffold including a plurality of rows of loops and a plurality of rows of rungs arranged around the central longitudinal axis in an alternating fashion; and a polymeric covering extending along the tubular scaffold. Each row of loops may extend longitudinally along the tubular scaffold between the proximal end and the distal end. Each row of rungs may extend longitudinally along the tubular scaffold between the proximal end and the distal end. The tubular scaffold may include a first cutout region extending along a majority of the length of the tubular scaffold and defining a first proximal end oriented toward the proximal end of the tubular scaffold and a first distal end oriented toward the distal end of the tubular scaffold, and a second cutout region extending along a majority of the length of the tubular scaffold and defining a second proximal end oriented toward the proximal end of the tubular scaffold and a second distal end oriented toward the distal end of the tubular scaffold. The polymeric covering may be uninterrupted along the first cutout region and the second cutout region.

In addition or alternatively to any example described herein, the first cutout region is formed by removing a medial portion of a first row of loops and medial portions of rows of rungs immediately adjacent to the first row of loops along the majority of the length of the tubular scaffold.

In addition or alternatively to any example described herein, forming the first cutout region causes the single filament to be discontinuous within the first cutout region.

In addition or alternatively to any example described herein, the discontinuous single filament comprises a first plurality of terminal ends extending along the first cutout region.

In addition or alternatively to any example described herein, the second cutout region is formed by removing a medial portion of a second row of loops and medial portions of rows of rungs immediately adjacent to the second row of loops along the majority of the length of the tubular scaffold.

In addition or alternatively to any example described herein, forming the second cutout region causes the single filament to be discontinuous within the second cutout region.

In addition or alternatively to any example described herein, the discontinuous single filament comprises a second plurality of terminal ends extending along the second cutout region.

In addition or alternatively to any example described herein, the second cutout region is circumferentially spaced apart from the first cutout region.

In addition or alternatively to any example described herein, the first proximal end and the second proximal end are disposed distal of the proximal end of the tubular scaffold. The first distal end and the second distal end are disposed proximal of the distal end of the tubular scaffold.

In addition or alternatively to any example described herein, the first cutout region extends along at least 60% of the length of the tubular scaffold.

In addition or alternatively to any example described herein, the first cutout region extends along at least 75% of the length of the tubular scaffold.

In addition or alternatively to any example described herein, a method of making an endoprosthesis configured to shift between a collapsed configuration and an expanded configuration may comprise: knitting a tubular scaffold from a single filament, the tubular scaffold including a plurality of rows of loops and a plurality of rows of rungs arranged around a central longitudinal axis in an alternating fashion; heat setting the tubular scaffold in the expanded configuration; after the heat setting step, removing a medial portion of a first row of loops and medial portions of rows of rungs immediately adjacent to the first row of loops along a majority of a length of the tubular scaffold to form a first cutout region; and after the removing step, applying a polymeric covering to the tubular scaffold, wherein the polymeric covering is uninterrupted along the first cutout region.

In addition or alternatively to any example described herein, the method may further comprise: after the heat setting step, removing a medial portion of a second row of loops and medial portions of rows of rungs immediately adjacent to the second row of loops along the majority of the length of the tubular scaffold to form a second cutout region.

In addition or alternatively to any example described herein, the second cutout region is circumferentially spaced apart from the first cutout region.

In addition or alternatively to any example described herein, forming the first cutout region causes the single filament to be discontinuous within the first cutout region.

In addition or alternatively to any example described herein, the discontinuous single filament comprises a first plurality of terminal ends extending along the first cutout region. The first plurality of terminal ends is embedded within the polymeric covering.

In addition or alternatively to any example described herein, an endoprosthesis configured to shift between a collapsed configuration and an expanded configuration may comprise a tubular scaffold formed from a single filament knitted about a central longitudinal axis and defining a length from a proximal end to a distal end, the tubular scaffold including a plurality of rows of loops and a plurality of rows of rungs arranged around the central longitudinal axis in an alternating fashion; and a polymeric covering extending along the tubular scaffold. Each row of loops may extend longitudinally along the tubular scaffold between the proximal end and the distal end. each row of rungs may extend longitudinally along the tubular scaffold between the proximal end and the distal end. A first row of loops of the plurality of rows of loops may be discontinuous along a medial region of the tubular scaffold and rows of rungs on circumferentially opposite sides of the first row of loops may be discontinuous along the medial region of the tubular scaffold. A second row of loops of the plurality of rows of loops circumferentially opposite the first row of loops may be discontinuous along the medial region of the tubular scaffold and rows of rungs on opposite sides of the second row of loops may be discontinuous along the medial region of the tubular scaffold. The polymeric covering may be continuous along the medial region of the tubular scaffold. The polymeric covering may be formed from silicone. The medial region may extend along at least 60% of the length of the tubular scaffold.

In addition or alternatively to any example described herein, within the medial region the single filament comprises a plurality of discontinuous segments.

In addition or alternatively to any example described herein, the plurality of discontinuous segments forms a plurality of terminal ends along the medial region, the plurality of terminal ends being embedded within the polymeric covering.

In addition or alternatively to any example described herein, the endoprosthesis is self-biased toward the expanded configuration.

The above summary of some embodiments, aspects, and/or examples is not intended to describe each disclosed embodiment or every implementation of the present disclosure. The Figures, and Detailed Description, which follow, more particularly exemplify these embodiments.

BRIEF DESCRIPTION OF THE DRAWINGS

The disclosure may be more completely understood in consideration of the following detailed description in connection with the accompanying drawings, in which.

Figure 1:
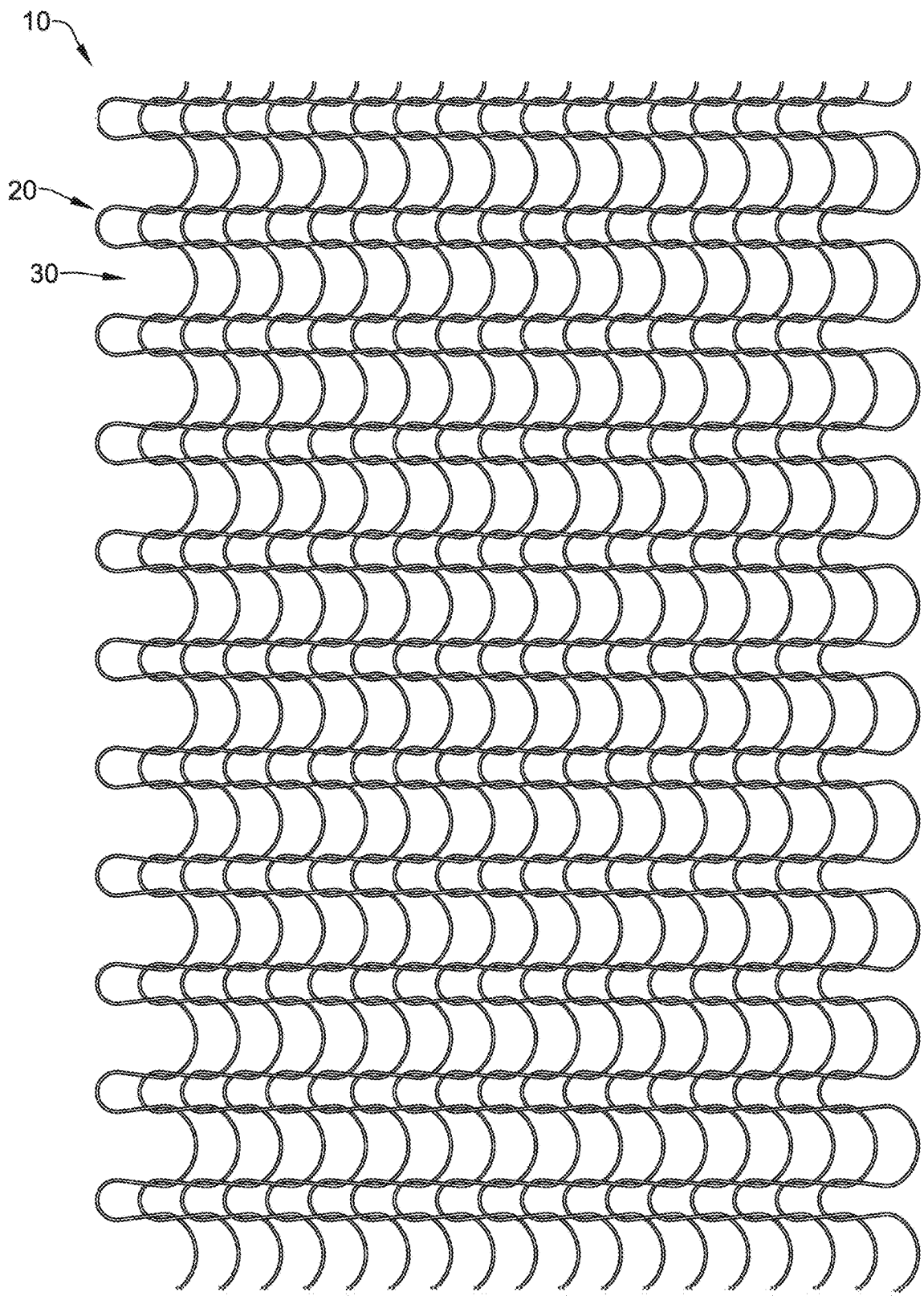
FIG. 1 illustrates a prior art knitted stent.

While aspects of the disclosure are amenable to various modifications and alternative forms, specifics thereof have been shown by way of example in the drawings and will be described in detail. It should be understood, however, that the intention is not to limit aspects of the disclosure to the particular embodiments described. On the contrary, the intention is to cover all modifications, equivalents, and alternatives falling within the spirit and scope of the disclosure.

DETAILED DESCRIPTION

The following description should be read with reference to the drawings, which are not necessarily to scale, wherein like reference numerals indicate like elements throughout the several views. The detailed description and drawings are intended to illustrate but not limit the disclosure. Those skilled in the art will recognize that the various elements described and/or shown may be arranged in various combinations and configurations without departing from the scope of the disclosure. The detailed description and drawings illustrate example embodiments of the disclosure.

For the following defined terms, these definitions shall be applied, unless a different definition is given in the claims or elsewhere in this specification.

All numeric values are herein assumed to be modified by the term "about," whether or not explicitly indicated. The term "about", in the context of numeric values, generally refers to a range of numbers that one of skill in the art would consider equivalent to the recited value (e.g., having the same function or result). In many instances, the term "about" may include numbers that are rounded to the nearest significant figure. Other uses of the term "about" (e.g., in a context other than numeric values) may be assumed to have their ordinary and customary definition(s), as understood from and consistent with the context of the specification, unless otherwise specified.

The recitation of numerical ranges by endpoints includes all numbers within that range, including the endpoints (e.g., 1 to 5 includes 1, 1.5, 2, 2.75, 3, 3.80, 4, and 5).

Although some suitable dimensions, ranges, and/or values pertaining to various components, features and/or specifications are disclosed, one of skill in the art, incited by the present disclosure, would understand desired dimensions, ranges, and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise. It is to be noted that in order to facilitate understanding, certain features of the disclosure may be described in the singular, even though those features may be plural or recurring within the disclosed embodiment(s). Each instance of the features may include and/or be encompassed by the singular disclosure(s), unless expressly stated to the contrary. For simplicity and clarity purposes, not all elements of the disclosure are necessarily shown in each figure or discussed in detail below. However, it will be understood that the following discussion may apply equally to any and/or all of the components for which there are more than one, unless explicitly stated to the contrary. Additionally, not all instances of some elements or features may be shown in each figure for clarity.

Relative terms such as "proximal", "distal", "advance", "retract", variants thereof, and the like, may be generally considered with respect to the positioning, direction, and/or operation of various elements relative to a user/operator/manipulator of the device, wherein "proximal" and "retract" indicate or refer to closer to or toward the user and "distal" and "advance" indicate or refer to farther from or away from the user. In some instances, the terms "proximal" and "distal" may be arbitrarily assigned in an effort to facilitate understanding of the disclosure, and such instances will be readily apparent to the skilled artisan. Other relative terms, such as "upstream", "downstream", "inflow", and "outflow" refer to a direction of fluid flow within a lumen, such as a body lumen, a blood vessel, or within a device. Still other relative terms, such as "axial", "circumferential", "longitudinal", "lateral", "radial", etc. and/or variants thereof generally refer to direction and/or orientation relative to a central longitudinal axis of the disclosed structure or device.

The term "extent" may be understood to mean a greatest measurement of a stated or identified dimension, unless the extent or dimension in question is preceded by or identified as a "minimum", which may be understood to mean a smallest measurement of the stated or identified dimension. For example, "outer extent" may be understood to mean an outer dimension, "radial extent" may be understood to mean a radial dimension, "longitudinal extent" may be understood to mean a longitudinal dimension, etc. Each instance of an "extent" may be different (e.g., axial, longitudinal, lateral, radial, circumferential, etc.) and will be apparent to the skilled person from the context of the individual usage. Generally, an "extent" may be considered a greatest possible dimension measured according to the intended usage, while a "minimum extent" may be considered a smallest possible dimension measured according to the intended usage. In some instances, an "extent" may generally be measured orthogonally within a plane and/or cross-section, but may be, as will be apparent from the particular context, measured differently—such as, but not limited to, angularly, radially, circumferentially (e.g., along an arc), etc.

The terms "monolithic" and "unitary" shall generally refer to an element or elements made from or consisting of a single structure or base unit/element. A monolithic and/or unitary element shall exclude structure and/or features made by assembling or otherwise joining multiple discrete structures or elements together.

It is noted that references in the specification to "an embodiment", "some embodiments", "other embodiments", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it would be within the knowledge of one skilled in the art to implement the particular feature, structure, or characteristic in connection with other embodiments, whether or not explicitly described, unless clearly stated to the contrary. That is, the various individual elements described below, even if not explicitly shown in a particular combination, are nevertheless contemplated as being combinable or arrangeable with each other to form other additional embodiments or to complement and/or enrich the described embodiment(s), as would be understood by one of ordinary skill in the art.

For the purpose of clarity, certain identifying numerical nomenclature (e.g., first, second, third, fourth, etc.) may be used throughout the description and/or claims to name and/or differentiate between various described and/or claimed features. It is to be understood that the numerical nomenclature is not intended to be limiting and is exemplary only. In some embodiments, alterations of and deviations from previously used numerical nomenclature may be made in the interest of brevity and clarity. That is, a feature identified as a "first" element may later be referred to as a "second" element, a "third" element, etc. or may be omitted entirely, and/or a different feature may be referred to as the "first" element. The meaning and/or designation in each instance will be apparent to the skilled practitioner.

The figures illustrate selected components and/or arrangements of an endoprosthesis or stent. It should be noted that in any given figure, some features of the endoprosthesis or stent may not be shown, or may be shown schematically, for simplicity. Additional details regarding some of the components of the endoprosthesis or stent may be illustrated in other figures in greater detail. It is to be noted that in order to facilitate understanding, certain features of the disclosure may be described in the singular, even though those features may be plural or recurring within the disclosed embodiment(s). Each instance of the features may include and/or be encompassed by the singular disclosure(s), unless expressly stated to the contrary. For example, a reference to "the filament", "the cell", "the strut", or other features may be equally referred to all instances and quantities beyond one of said feature. As such, it will be understood that the following discussion may apply equally to any and/or all of the components for which there are more than one within the endoprosthesis or stent, unless explicitly stated to the contrary. Additionally, not all instances of some elements or features may be shown in each figure for clarity.

In some patients, a stricture may form or develop that may partially or completely block a body lumen such as the trachea, the esophagus, the common bile duct, the pancreatic duct, etc., thus requiring treatment. It will be appreciated that this disclosure may be directed to features that facilitate and/or permit treatment of body lumens.

Figure 2:
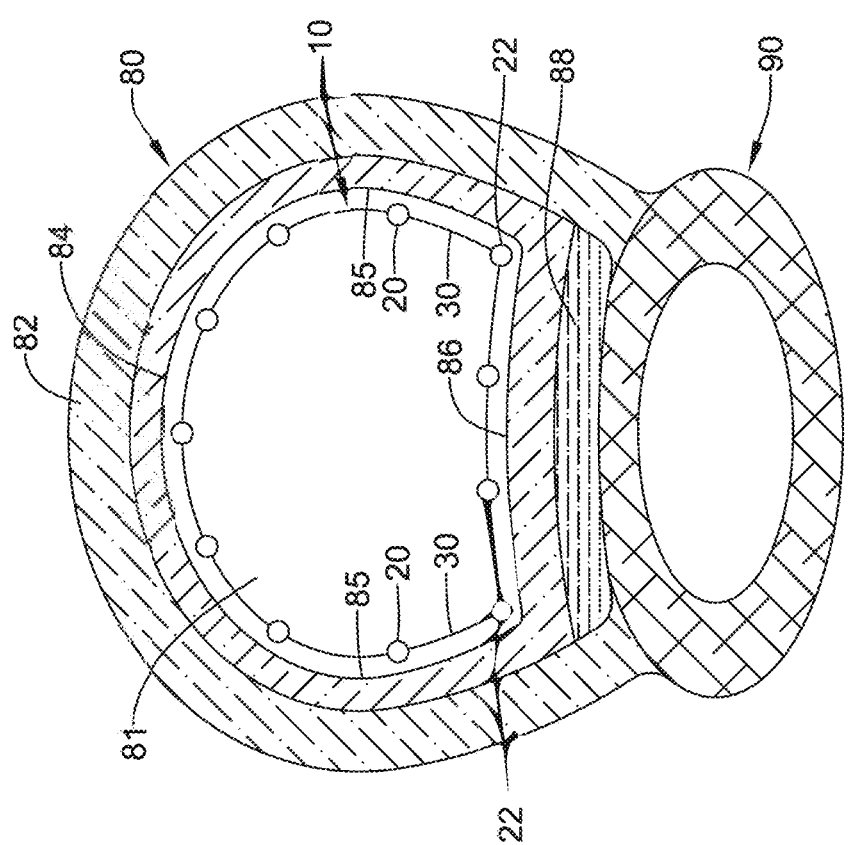
FIG. 2 illustrates a cross-section of a portion of a patient's trachea with the prior art knitted stent implanted therein.

A prior art knitted stent 10 is illustrated in FIG. 1. The prior art knitted stent 10 has been used to treat body lumens. The prior art knitted stent 10 may include a plurality of spines 20 and a plurality of rungs 30 interposed between adjacent spines of the plurality of spines 20. The prior art knitted stent 10 may be formed from one continuous wire. When unconstrained, the prior art knitted stent 10 may have a generally circular cross-sectional shape and/or extent. When placed in the anatomy for treatment, the prior art knitted stent 10 may be flexible enough to approximate the shape of the body lumen in which it is implanted, as seen in FIG. 2 for example, which illustrates a cross-section of a portion of a patient's trachea 80 with the prior art knitted stent 10 implanted therein.

The trachea 80 is a passage that enables air to travel between the oral and nasal cavities into the bronchi, in order to reach the lungs during breathing. The trachea 80 may include an anterior wall 84, a posterior wall 86, and lateral walls 85 extending between the anterior wall 84 and the posterior wall 86. The trachea 80 may have an elongated D-shaped cross-section with the flat posterior wall 86. When implanted, the prior art knitted stent 10 may naturally settle into the lumen 81 of the trachea 80 with spines (e.g., corner spines 22) of the plurality of spines 20 positioned adjacent the flat posterior wall 86.

Figure 3:
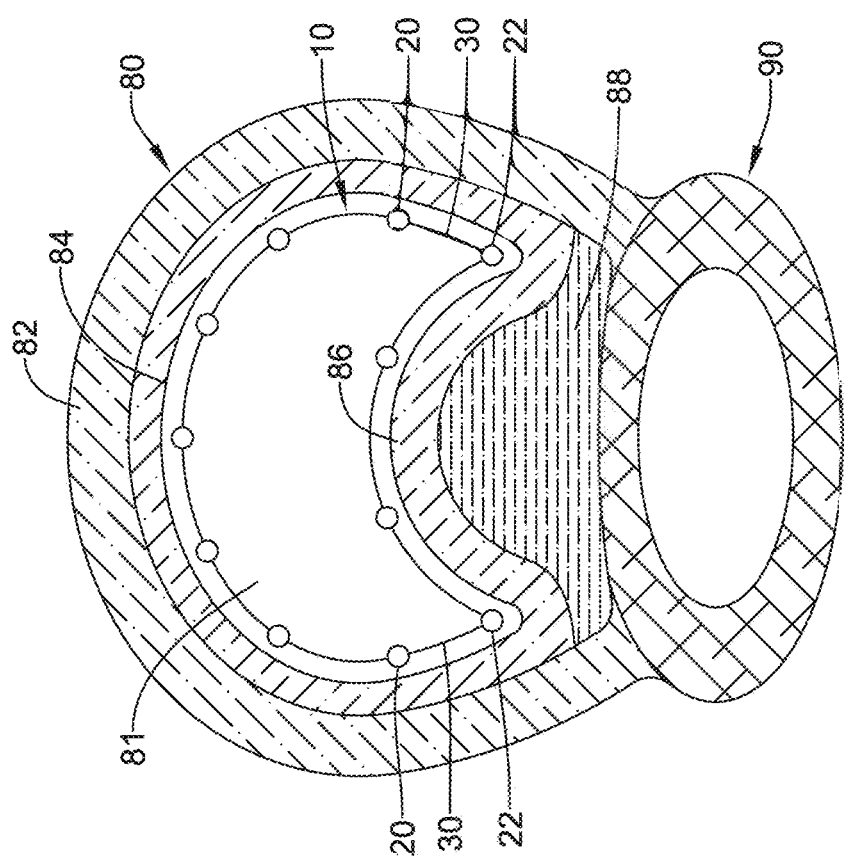
FIG. 3 illustrates the implanted prior art knitted stent of FIG. 2 subjected to forced inspiration/expiration and/or coughing.

Several C-shaped bars of the hyaline cartilage 82 prevent the trachea 80 from collapsing. The posterior wall 86 includes a trachealis muscle 88 that constricts into the lumen 81 of the trachea 80 to narrow the airway in order expel air from the trachea 80 during a cough, as shown in FIG. 3, and the anterior wall 84 includes cartilage rings. The trachea 80 is oriented anterior to the esophagus 90, with the trachealis muscle 88 positioned between the lumen 81 of the trachea 80 and the esophagus 90.

FIG. 3 illustrates how during forced inspiration/expiration and/or coughing the lumen 81 of the trachea 80 is deformed by the trachealis muscle 88 constricting into the lumen 81. Sharp fold lines for formed in lateral corners of the lumen 81 adjacent the posterior wall 86 resulting in a crescent shape. The implanted stent 10 will deform in a similar manner causing areas of high stress in the corner spines 22 and eventually possible stent fractures along the sharp fold lines and/or the corner spines 22.

Figure 4:
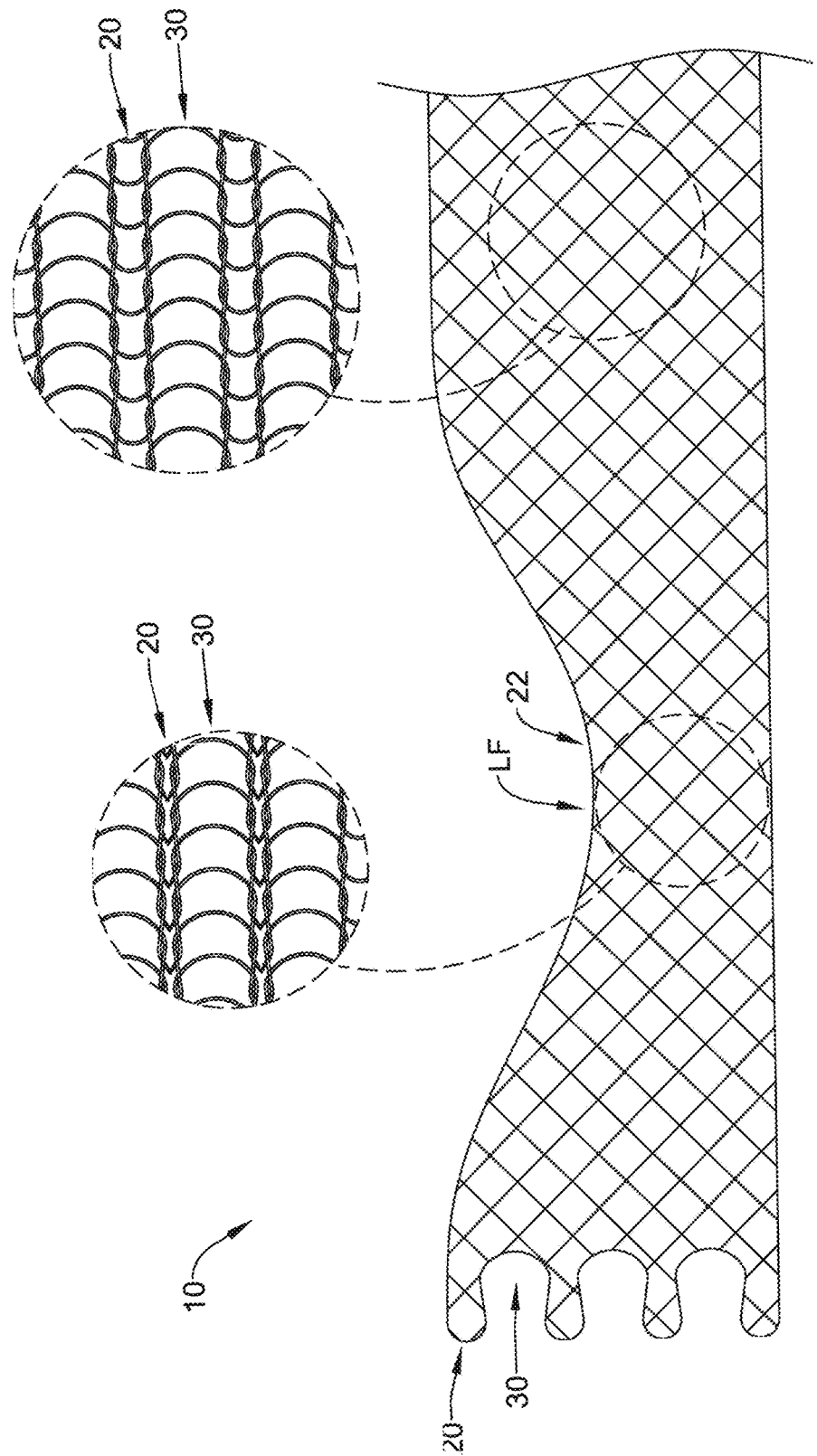
FIG. 4 illustrates the prior art stent of FIG. 1 subjected to a lateral compressive force.

FIG. 4 illustrates a side view of the prior art knitted stent 10 subjected to a lateral force LF, as would occur during inspiration/expiration and/or coughing. A portion of the prior art knitted stent 10 is deflected inward along the corner spines 22. This portion travels longitudinally along the length of the prior art knitted stent 10 as the lateral force LF moves, as would occur during forced inspiration/expiration and/or coughing. As such, the areas of high stress would not be limited to a single portion the knitted stent 10 but would instead extend along the length of the knitted stent 10.

Figure 5:
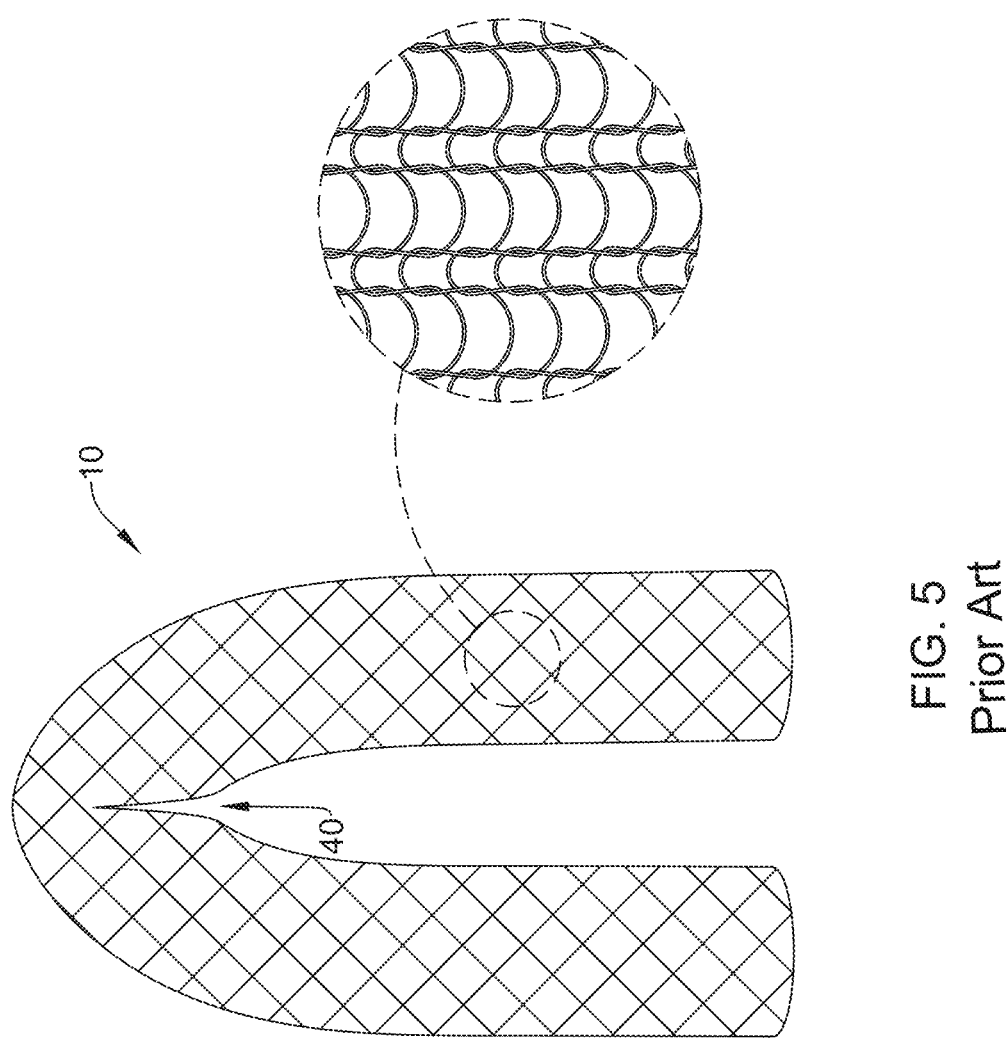
FIG. 5 illustrates the prior art stent of FIG. 1 suffering kinking after being subjected to a bending force.

In another example, FIG. 5 illustrates the prior art knitted stent 10 bent almost in half (approximately 180 degrees), to show kinking that may occur at severe bends in the anatomy due to limited flexibility of the prior art knitted stent 10. The knitted pattern of the stent 10 does not allow for stretching over the outside of the bend or compression at the inside of the bend, thus the stent 10 forms a kink 40 at the bend. As the knitted pattern contains spines that run parallel to the stent (as seen in FIG. 1), there is build-up of material at the bend, which causes the stent 10 to kink. The kinking tendency shown in FIG. 5 limits the flexibility and/or the bending capability of the prior art knitted stent 10.

Figure 6:
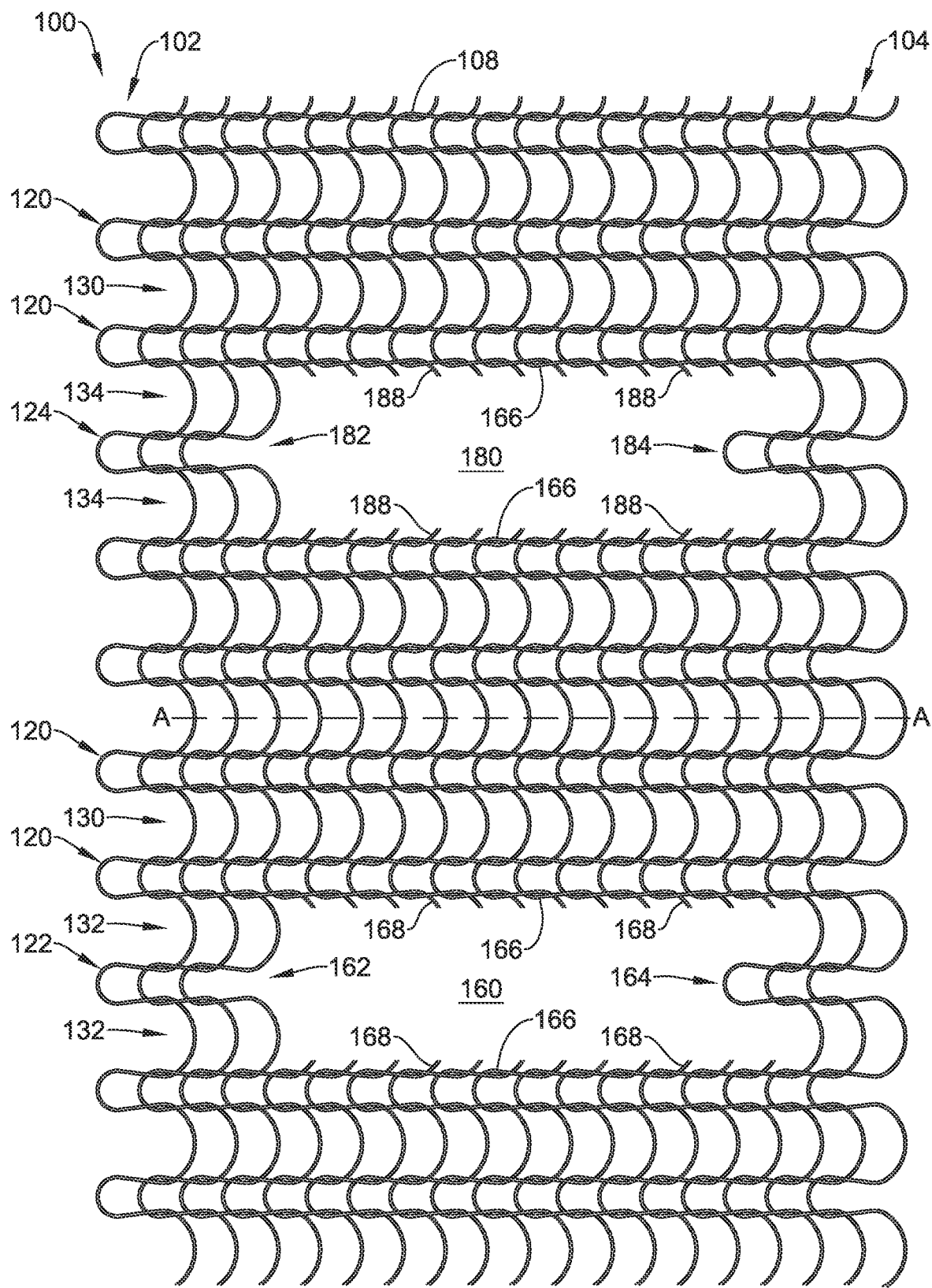
FIG. 6 illustrates aspects of an endoprosthesis according to the disclosure.

FIG. 6 illustrates aspects of an endoprosthesis 100 designed and configured to address shortcomings of the prior art knitted stent 10. The term "endoprosthesis" may be used interchangeably with the term "stent" herein. For ease of illustration, the endoprosthesis 100 is shown in a flat pattern configuration. The endoprosthesis 100 may comprise a tubular scaffold 108 formed from a single filament knitted about a central longitudinal axis A and defining a length from a proximal end 102 to a distal end 104.

The endoprosthesis 100 and/or the tubular scaffold 108 may be configured to shift between a collapsed configuration and an expanded configuration. The collapsed configuration may be a configuration in which the endoprosthesis 100 is axially elongated and/or radially collapsed or compressed compared to the expanded configuration. The expanded configuration may be a configuration in which the endoprosthesis 100 is axially shortened and/or radially expanded compared to the collapsed configuration. In at least some embodiments, the endoprosthesis 100 and/or the tubular scaffold 108 may be self-expandable. For example, the endoprosthesis 100 and/or the tubular scaffold 108 may be formed from a shape memory material. In some embodiments, the endoprosthesis 100 and/or the tubular scaffold 108 may be mechanically expandable. For example, the endoprosthesis 100 and/or the tubular scaffold 108 may be expandable using an inflatable balloon, using an actuation member, or other suitable means. During delivery to a treatment site, the endoprosthesis 100 and/or the tubular scaffold 108 may be disposed within a lumen of a delivery sheath in the collapsed configuration. Upon removal from the lumen of the delivery sheath, the endoprosthesis 100 and/or the tubular scaffold 108 may shift and/or may be shifted from the collapsed configuration to the expanded configuration.

The tubular scaffold 108 may include and/or be formed with a plurality of cells. In some embodiments, the tubular scaffold 108 may include and/or be formed from the single filament interwoven around the central longitudinal axis of the endoprosthesis 100 and/or the tubular scaffold 108. In at least some embodiments, the single filament may form and/or define the plurality of cells. In some embodiments, the tubular scaffold 108 may be braided, knitted, or woven from the single filament. In some embodiments, the single filament may be a wire, a thread, a strand, etc. In some embodiments, adjacent portions of the single filament may define openings or interstices through a wall of the tubular scaffold 108. Alternatively, in some embodiments, the tubular scaffold 108 may be a monolithic structure formed from a cylindrical tubular member, such as a single, cylindrical laser-cut nickel-titanium (e.g., Nitinol) tubular member, in which the remaining (e.g., unremoved) portions of the tubular member form the tubular scaffold 108 with openings or interstices defined therebetween.

The tubular scaffold 108 may be substantially tubular and/or may include a lumen extending axially therethrough along the central longitudinal axis A of the tubular scaffold 108. In some embodiments, the tubular scaffold 108 may have an axial length of about 40 millimeters to about 250 millimeters, about 50 millimeters to about 225 millimeters, about 60 millimeters to about 200 millimeters, about 80 millimeters to about 175 millimeters, about 100 millimeters to about 150 millimeters, or another suitable range. In some embodiments, the tubular scaffold 108 may have a radial outer dimension or radial extent of about 5 millimeters to about 30 millimeters, about 6 millimeters to about 25 millimeters, about 8 millimeters to about 20 millimeters, about 10 millimeters to about 15 millimeters, or another suitable range. Other configurations are also contemplated. Some suitable but non-limiting materials for the endoprosthesis 100, the tubular scaffold 108, and/or components or elements thereof, for example metallic materials and/or polymeric materials, are described below.

The tubular scaffold 108 may include a plurality of rows of loops 120 and a plurality of rows of rungs 130 arranged around the central longitudinal axis A in an alternating fashion. For example, one row of loops may be disposed between two adjacent rows of rungs and one row of rungs may be disposed between two adjacent rows of loops. The plurality of rows of rungs 130 may be more flexible than the plurality of rows of loops 120 and as such may provide flexibility to the tubular scaffold 108 as a whole. In some embodiments, each of the plurality of rows of rungs 130 may extend a greater circumferential distance around the tubular scaffold 108 than each of the plurality of rows of loops 120. Other configurations are also contemplated. In some embodiments, the tubular scaffold 108, the single filament, and/or the plurality of rows of loops 120 and the plurality of rows of rungs 130 may be heat set in the expanded configuration such that the endoprosthesis 100 and/or the tubular scaffold 108 is self-biased toward the expanded configuration.

Each row of loops of the plurality of rows of loops 120 may extend longitudinally along the tubular scaffold 108 between the proximal end 102 and the distal end 104. In some embodiments, at least some of the rows of loops of the plurality of rows of loops 120 may extend continuously from the proximal end 102 to the distal end 104. In some embodiments, some of the rows of loops of the plurality of rows of loops 120 may be discontinuous between the proximal end 102 and the distal end 104. Each row of rungs of the plurality of rows of rungs 130 may extend longitudinally along the tubular scaffold 108 between the proximal end 102 and the distal end 104. In some embodiments, at least some of the rows of rungs of the plurality of rows of rungs 130 may extend continuously from the proximal end 102 to the distal end 104. In some embodiments, some of the rows of rungs of the plurality of rows of rungs 130 may be discontinuous between the proximal end 102 and the distal end 104.

In some embodiments, each loop of the plurality of rows of loops 120 may extend about 0.05 millimeters (mm), 0.10 mm, 0.15 mm, 0.25 mm, 0.5 mm, 0.75 mm, 1 mm, 2 mm, 3 mm, etc. around the circumference (e.g., along an arc) of the tubular scaffold 108. In some embodiments, each rung of the plurality of rows of rungs 130 may extend about 0.10 millimeters (mm), 0.15 mm, 0.25 mm, 0.5 mm, 0.75 mm, 1 mm, 2 mm, 3 mm, 4 mm, 5 mm, etc. around the circumference (e.g., along an arc) of the tubular scaffold 108. Other configurations are also contemplated.

The tubular scaffold 108 may include a first cutout region 160 extending along a majority of the length of the tubular scaffold 108. In some embodiments, the first cutout region 160 may extend along at least 60% of the length of the tubular scaffold 108. In some embodiments, the first cutout region 160 may extend along at least 70% of the length of the tubular scaffold 108. In some embodiments, the first cutout region 160 may extend along at least 75% of the length of the tubular scaffold 108. In some embodiments, the first cutout region 160 may extend along at least 80% of the length of the tubular scaffold 108. In some embodiments, the first cutout region 160 may extend along at least 85% of the length of the tubular scaffold 108. In some embodiments, the first cutout region 160 may extend along at least 90% of the length of the tubular scaffold 108. Other configurations are also contemplated.

The first cutout region 160 may be disposed between the proximal end 102 of the tubular scaffold 108 and the distal end 104 of the tubular scaffold 108. The first cutout region 160 may define and extend continuously from a first proximal end 162 oriented toward the proximal end 102 of the tubular scaffold 108 and a first distal end 164 oriented toward the distal end 104 of the tubular scaffold 108. In some embodiments, the first proximal end 162 may be disposed distal of the proximal end 102 of the tubular scaffold 108. In some embodiments, the first distal end 164 may be disposed proximal of the distal end 104 of the tubular scaffold 108.

In some embodiments, the first cutout region 160 may be formed by removing a medial portion of a first row of loops 122 of the plurality of rows of loops 120 and medial portions of rows of rungs 132 of the plurality of rows of rungs 130 immediately adjacent to the first row of loops 122 along the majority of the length of the tubular scaffold 108. In some embodiments, the first row of loops 122 of the plurality of rows of loops 120 may be discontinuous along a medial region of the tubular scaffold 108 and rows of rungs 132 on opposite sides of the first row of loops 122 in a circumferential direction from the first row of loops 122 are discontinuous along the medial region of the tubular scaffold 108.

The medial region of the tubular scaffold 108 may extend along a majority of the length of the tubular scaffold 108. In some embodiments, the medial region of the tubular scaffold 108 may extend along at least 60% of the length of the tubular scaffold 108. In some embodiments, the medial region of the tubular scaffold 108 may extend along at least 70% of the length of the tubular scaffold 108. In some embodiments, the medial region of the tubular scaffold 108 may extend along at least 75% of the length of the tubular scaffold 108. In some embodiments, the medial region of the tubular scaffold 108 may extend along at least 80% of the length of the tubular scaffold 108. In some embodiments, the medial region of the tubular scaffold 108 may extend along at least 85% of the length of the tubular scaffold 108. In some embodiments, the medial region of the tubular scaffold 108 may extend along at least 90% of the length of the tubular scaffold 108. Other configurations are also contemplated.

The first cutout region 160 may be formed after heat setting the tubular scaffold 108, the single filament, and/or the plurality of rows of loops 120 and the plurality of rows of rungs 130. In at least some embodiments, forming the first cutout region 160 may cause the single filament to be discontinuous within the first cutout region 160 and/or along the length of the tubular scaffold 108. Similarly, forming the first cutout region 160 may cause the first row of loops 122 and rows of rungs 132 immediately adjacent the first row of loops 122 to be discontinuous within the first cutout region 160 and/or along the length of the tubular scaffold 108. In some embodiments, within the medial region of the tubular scaffold 108 the single filament may comprise a plurality of discontinuous segments 166.

The discontinuous single filament may comprise and/or the plurality of discontinuous segments 166 may form a first plurality of terminal ends 168 extending along the first cutout region 160 and/or the medial region. The first plurality of terminal ends 168 may be in close proximity to one of the plurality of rows of loops 120 and/or a perimeter of the first cutout region 160. For example, the first plurality of terminal ends 168 may be within about 0.01 millimeters (mm), 0.02 mm, 0.03 mm, 0.05 mm, 0.07 mm, 0.10 mm, 0.15 mm, 0.25 mm, 0.5 mm, 0.75 mm, 1 mm, etc. of one of the plurality of rows of loops 120. Since the tubular scaffold 108, the single filament, and/or the plurality of rows of loops 120 and the plurality of rows of rungs 130 were heat set prior to forming the first cutout region 160 and/or prior to removing the medial portion of the first row of loops 122 of the plurality of rows of loops 120 and medial portions of rows of rungs 132 of the plurality of rows of rungs 130 immediately adjacent to the first row of loops 122 along the majority of the length of the tubular scaffold 108, the tubular scaffold 108 is prevented from unraveling even when the medial portion(s) is removed and/or the first cutout region 160 is formed.

In some embodiments, the first cutout region 160 may be formed by removing several adjacent rows of loops of the plurality of rows of loops 120 and rows of rungs immediately adjacent the several adjacent rows of loops. In one example, the first cutout region 160 may be formed by removing two adjacent rows of loops, the row of rungs disposed between the two adjacent rows of loops, and the rows of rungs on either circumferential side of the two adjacent rows of loops. In another example, the first cutout region 160 may be formed by removing three adjacent rows of loops, the two rows of rungs disposed between the three adjacent rows of loops, and the rows of rungs on either circumferential side of the three adjacent rows of loops. Other configurations are also contemplated.

In some embodiments, the tubular scaffold 108 may include a second cutout region 180 extending along a majority of the length of the tubular scaffold 108. In some embodiments, the second cutout region 180 may extend along at least 60% of the length of the tubular scaffold 108. In some embodiments, the second cutout region 180 may extend along at least 70% of the length of the tubular scaffold 108. In some embodiments, the second cutout region 180 may extend along at least 75% of the length of the tubular scaffold 108. In some embodiments, the second cutout region 180 may extend along at least 80% of the length of the tubular scaffold 108. In some embodiments, the second cutout region 180 may extend along at least 85% of the length of the tubular scaffold 108. In some embodiments, the second cutout region 180 may extend along at least 90% of the length of the tubular scaffold 108. Other configurations are also contemplated.

The second cutout region 180 may be disposed between the proximal end 102 of the tubular scaffold 108 and the distal end 104 of the tubular scaffold 108. The second cutout region 180 may define and extend continuously from a second proximal end 182 oriented toward the proximal end 102 of the tubular scaffold 108 and a second distal end 184 oriented toward the distal end 104 of the tubular scaffold 108. In some embodiments, the second proximal end 182 may be disposed distal of the proximal end 102 of the tubular scaffold 108. In some embodiments, the second distal end 184 may be disposed proximal of the distal end 104 of the tubular scaffold 108. In some embodiments, the second cutout region 180 may be circumferentially spaced apart from the first cutout region 160. In some embodiments, the second cutout region 180 may be disposed on an opposite side of the tubular scaffold 108 from the first cutout region 160 relative to the central longitudinal axis A.

In some embodiments, the second cutout region 180 may be formed by removing a medial portion of a second row of loops 124 of the plurality of rows of loops 120 and medial portions of rows of rungs 134 of the plurality of rows of rungs 130 immediately adjacent to the second row of loops 124 along the majority of the length of the tubular scaffold 108. The second row of loops 124 of the plurality of rows of loops 120 may be circumferentially spaced apart from the first row of loops 122 of the plurality of rows of loops 120. In some embodiments, the second row of loops 124 of the plurality of rows of loops 120 may be disposed on an opposite side of the tubular scaffold 108 from the first row of loops 122 of the plurality of rows of loops 120 relative to the central longitudinal axis A. In some embodiments, the second row of loops 124 of the plurality of rows of loops 120 may be circumferentially opposite the first row of loops 122 of the plurality of rows of loops 120. In some embodiments, the second row of loops 124 of the plurality of rows of loops 120 may be discontinuous along the medial region of the tubular scaffold 108 and rows of rungs 134 on opposite sides of the second row of loops 124 in a circumferential direction from the second row of loops 124 are discontinuous along the medial region of the tubular scaffold 108.

The medial region of the tubular scaffold 108 may extend along a majority of the length of the tubular scaffold 108. In some embodiments, the medial region of the tubular scaffold 108 may extend along at least 60% of the length of the tubular scaffold 108. In some embodiments, the medial region of the tubular scaffold 108 may extend along at least 70% of the length of the tubular scaffold 108. In some embodiments, the medial region of the tubular scaffold 108 may extend along at least 75% of the length of the tubular scaffold 108. In some embodiments, the medial region of the tubular scaffold 108 may extend along at least 80% of the length of the tubular scaffold 108. In some embodiments, the medial region of the tubular scaffold 108 may extend along at least 85% of the length of the tubular scaffold 108. In some embodiments, the medial region of the tubular scaffold 108 may extend along at least 90% of the length of the tubular scaffold 108. Other configurations are also contemplated.

The second cutout region 180 may be formed after heat setting the tubular scaffold 108, the single filament, and/or the plurality of rows of loops 120 and the plurality of rows of rungs 130. In at least some embodiments, forming the second cutout region 180 may cause the single filament to be discontinuous within the second cutout region 180 and/or along the length of the tubular scaffold 108. Similarly, forming the second cutout region 180 may cause the second row of loops 124 and rows of rungs 134 immediately adjacent the second row of loops 124 to be discontinuous within the second cutout region 180 and/or along the length of the tubular scaffold 108.

The discontinuous single filament may comprise and/or the plurality of discontinuous segments 166 may form a second plurality of terminal ends 188 extending along the second cutout region 180 and/or the medial region. The second plurality of terminal ends 188 may be in close proximity to one of the plurality of rows of loops 120 and/or a perimeter of the second cutout region 180. For example, the second plurality of terminal ends 188 may be within about 0.01 millimeters (mm), 0.02 mm, 0.03 mm, 0.05 mm, 0.07 mm, 0.10 mm, 0.15 mm, 0.25 mm, 0.5 mm, 0.75 mm, 1 mm, etc. of one of the plurality of rows of loops 120. Since the tubular scaffold 108, the single filament, and/or the plurality of rows of loops 120 and the plurality of rows of rungs 130 were heat set prior to forming the second cutout region 180 and/or prior to removing the medial portion of the second row of loops 124 of the plurality of rows of loops 120 and medial portions of rows of rungs 134 of the plurality of rows of rungs 130 immediately adjacent to the second row of loops 124 along the majority of the length of the tubular scaffold 108, the tubular scaffold 108 is prevented from unraveling even when the medial portion(s) is removed and/or the second cutout region 180 is formed.

In some embodiments, the second cutout region 180 may be formed by removing several adjacent rows of loops of the plurality of rows of loops 120 and rows of rungs immediately adjacent the several adjacent rows of loops. In one example, the second cutout region 180 may be formed by removing two adjacent rows of loops, the row of rungs disposed between the two adjacent rows of loops, and the rows of rungs on either circumferential side of the two adjacent rows of loops. In another example, the second cutout region 180 may be formed by removing three adjacent rows of loops, the two rows of rungs disposed between the three adjacent rows of loops, and the rows of rungs on either circumferential side of the three adjacent rows of loops. Other configurations are also contemplated.

Figure 7:
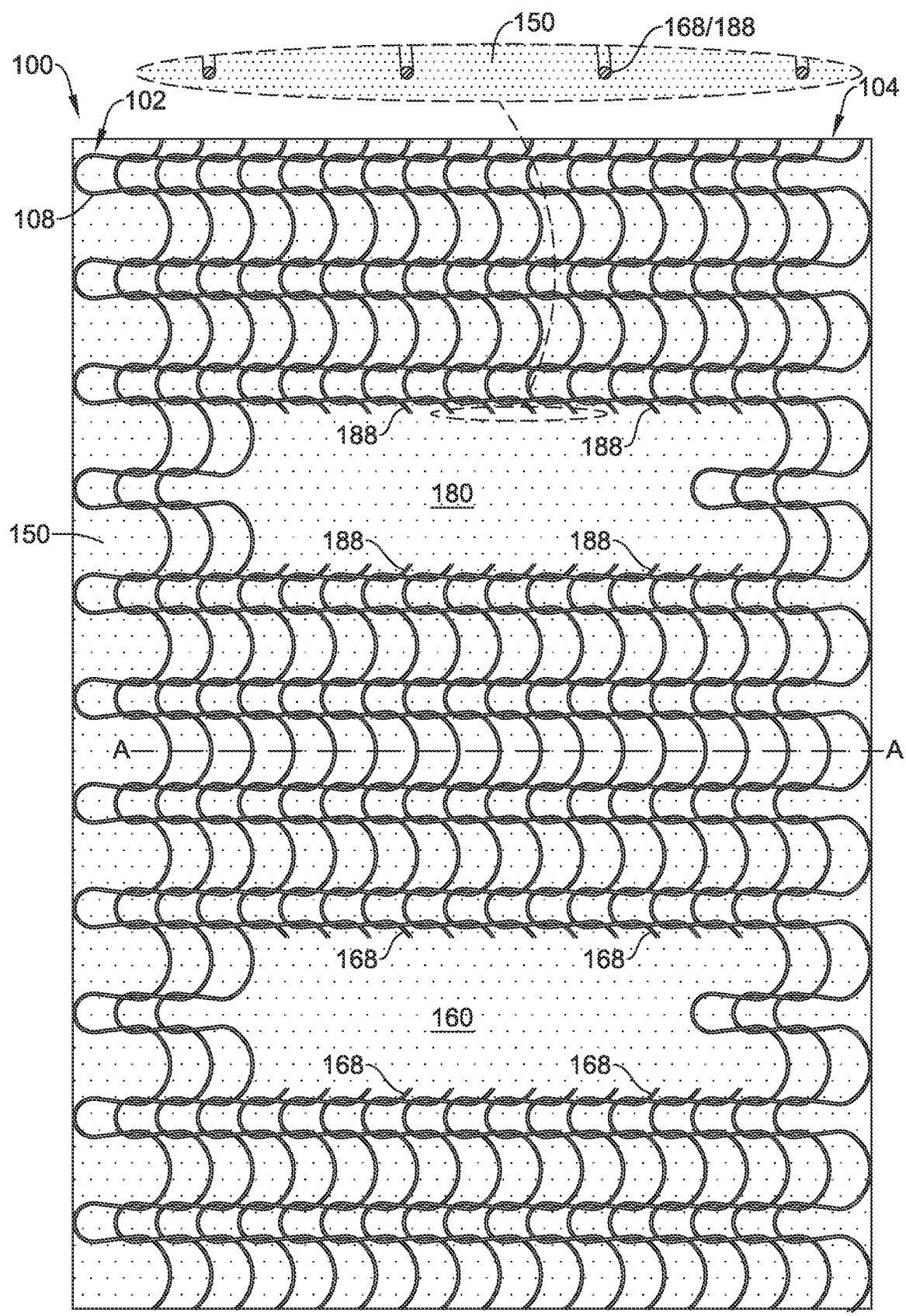
FIG. 7 illustrates aspects of the endoprosthesis of FIG. 6.

As shown in FIG. 7, the endoprosthesis 100 may include a polymeric covering 150 extending along the tubular scaffold 108. In some embodiments, the polymeric covering 150 may be fixedly secured to, bonded to, or otherwise attached about the entire circumference of the tubular scaffold 108. For example, the polymeric covering 150 may be continuously attached to the tubular scaffold 108 about its entire length, width, and/or circumference. In some embodiments, anywhere the polymeric covering 150 touches the tubular scaffold 108, the polymeric covering 150 may be fixedly secured to, bonded to, or otherwise attached to the tubular scaffold 108. In some embodiments, portions of the tubular scaffold 108 may be embedded within the polymeric covering 150. In some embodiments, the tubular scaffold 108 may be continuously and/or completely embedded within the polymeric covering 150.

In some embodiments, the polymeric covering 150 may be uninterrupted along and/or within the first cutout region 160. In some embodiments, the polymeric covering 150 may be uninterrupted along and/or within the second cutout region 180. In some embodiments, the polymeric covering 150 may be uninterrupted along and/or within the first cutout region 160 and the second cutout region 180. In some embodiments, the first plurality of terminal ends 168 and/or the second plurality of terminal ends 188 may be embedded within the polymeric covering 150, as shown in the cross-sectional detail view of FIG. 7. In some embodiments, the polymeric covering 150 may be continuous along the medial region of the tubular scaffold 108.

In some embodiments, the polymeric covering 150 may extend along an entire length of the endoprosthesis 100 and/or the tubular scaffold 108. In some embodiments, the polymeric covering 150 may extend along a portion of the length of the endoprosthesis 100 and/or the tubular scaffold 108. In some embodiments, the polymeric covering 150 may extend discontinuously between the proximal end 102 of the endoprosthesis 100 and/or the tubular scaffold 108 and the distal end 104 of the endoprosthesis 100 and/or the tubular scaffold 108. In some embodiments, the polymeric covering 150 may extend continuously from the proximal end 102 of the endoprosthesis 100 and/or the tubular scaffold 108 to the distal end 104 of the endoprosthesis 100 and/or the tubular scaffold 108. In some embodiments, all cells of the plurality of cells may be completely covered by the polymeric covering 150. Other configurations are also contemplated.

In use, when the endoprosthesis 100 is positioned within a body lumen, the polymeric covering 150 may form a substantially continuous outer covering disposed on and/or over the tubular scaffold 108, thereby forming a barrier, such as a sealed interface, between the lumen of the endoprosthesis 100 and/or the tubular scaffold 108 and the wall of the body lumen positioned radially outward of the polymeric covering 150. The polymeric covering 150 may isolate the lumen of the endoprosthesis 100 and/or the tubular scaffold 108 from the wall of the body lumen. The polymeric covering 150 may prevent tissue ingrowth into the lumen and/or the tubular scaffold 108 of the endoprosthesis 100 and thereby permit and/or aid removal of the endoprosthesis 100 and/or the tubular scaffold 108 from the body lumen. Some suitable examples of materials for the polymeric covering 150, including but not limited to PTFE, silicone, and the like, are discussed below.

Figure 8:
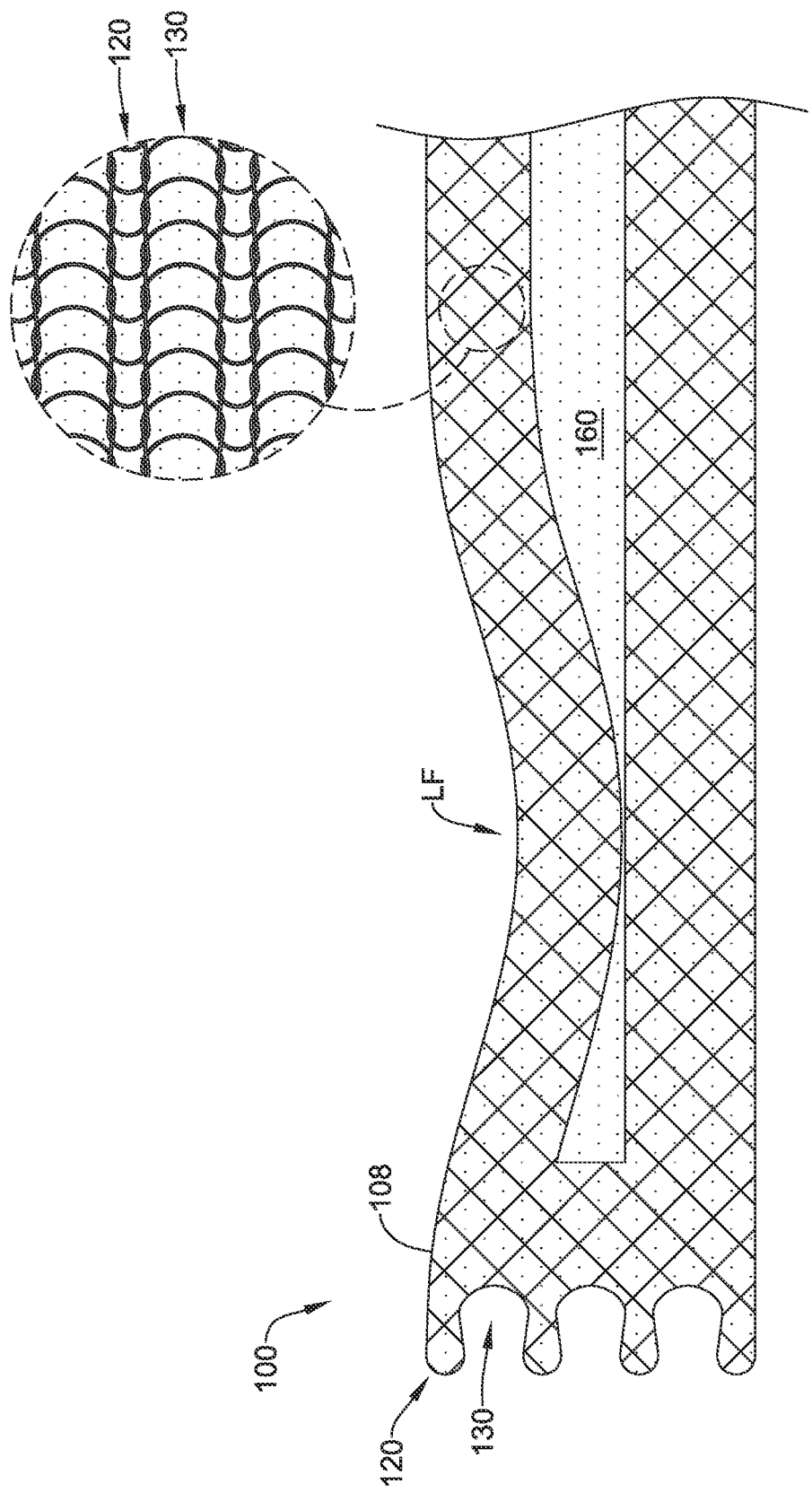
FIG. 8 illustrates the endoprosthesis of FIGS. 6-7 subjected to a lateral compressive force.

FIG. 8 illustrates a side view of the endoprosthesis 100 and/or the tubular scaffold 108 subjected to the lateral force LF, as would occur during inspiration/expiration and/or coughing, similar to the lateral force LF applied to the prior art knitted stent 10 in FIG. 4. As seen in FIG. 8, a portion of the endoprosthesis 100 and/or the tubular scaffold 108, and/or some of the plurality of rows of loops 120 and some of the plurality of rows of rungs 130, is deflected inward. This portion may travel longitudinally along the length of the endoprosthesis 100 and/or the tubular scaffold 108, as would occur during forced inspiration/expiration and/or coughing. The first cutout region 160 and/or the second cutout region 180 (not visible), and the polymeric covering 150, may permit the endoprosthesis 100 and/or the tubular scaffold 108 to deflect without incurring the same high stress concentrations that are found in the prior art knitted stent 10 of FIG. 4. The deformation found in the prior art knitted stent 10 of FIG. 4 is reduced or removed. Instead of outward stress being exerted on the single filament and/or the tubular scaffold 108 of the endoprosthesis 100, the endoprosthesis 100 and/or the tubular scaffold 108 may collapse in a generally uniform manner. The polymeric covering 150 may be flexible enough to allow the endoprosthesis 100 and/or the tubular scaffold 108 to absorb the stress is deform into a flattened orientation. Once the lateral force LF has been removed, the endoprosthesis 100 and/or the tubular scaffold 108 may return to its original orientation (e.g., the expanded configuration) and patency of the body lumen is maintained.

Figure 9:
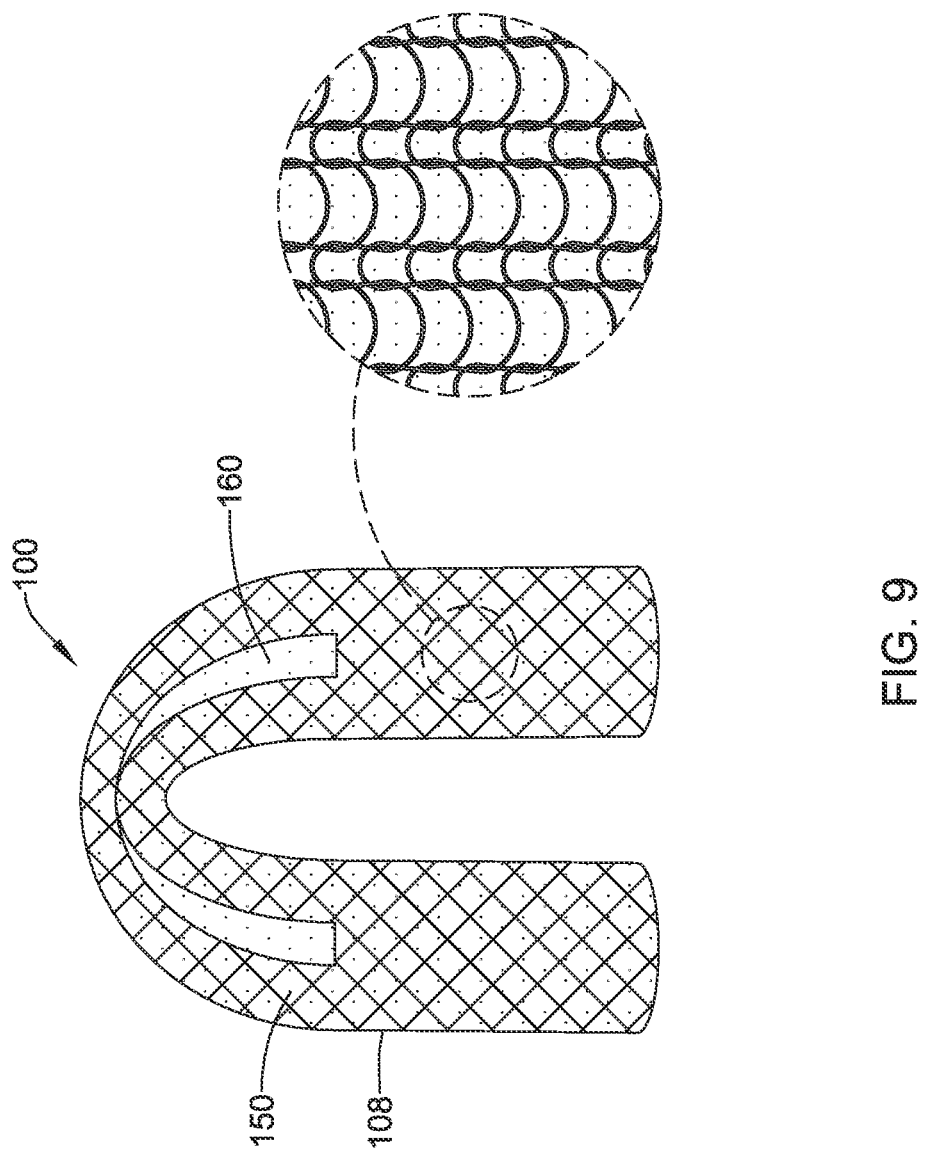
FIG. 9 illustrates the endoprosthesis of FIGS. 6-7 after being subjected to a bending force.

In another example, FIG. 9 illustrates the endoprosthesis 100 and/or the tubular scaffold 108 bent almost in half (approximately 180 degrees), to show that the kinking seen in the prior art knitted stent 10 of FIG. 5 is avoided. Testing of the endoprosthesis 100 has shown that the first cutout region 160, the second cutout region 180 (not visible), and/or the polymeric covering 150 improved the flexibility and kink resistance of the endoprosthesis 100 and/or the tubular scaffold 108 compared to the prior art knitted stent 10.

Figure 10:
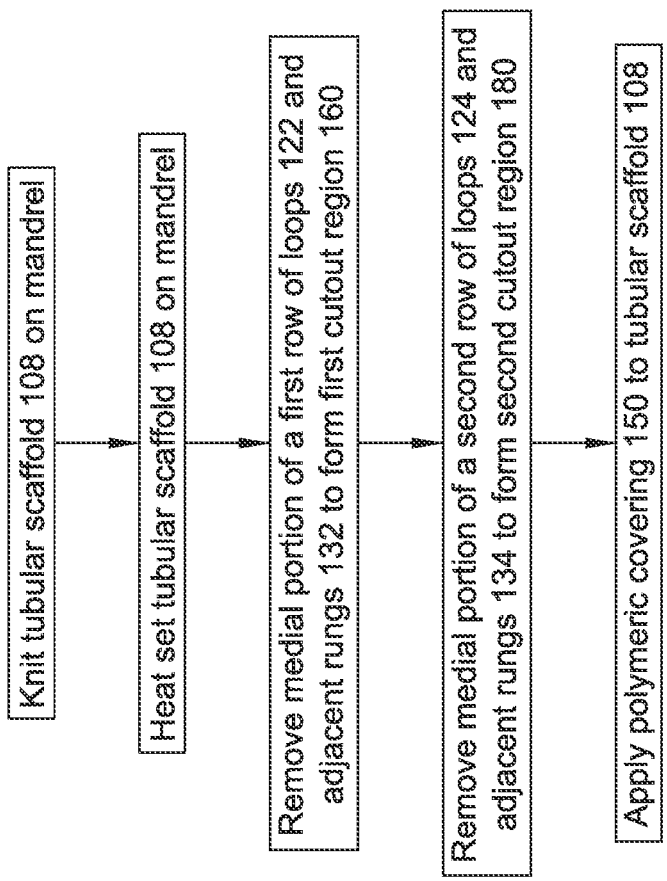
FIG. 10 illustrates aspects of a method of making an endoprosthesis according to the disclosure.

FIG. 10 illustrates aspects of a method of making the endoprosthesis 100. The method may include knitting the tubular scaffold 108 on a mandrel from a single filament, the tubular scaffold 108 including the plurality of rows of loops 120 and the plurality of rows of rungs 130 arranged around the central longitudinal axis A in an alternating fashion. In some embodiments, the mandrel may be generally cylindrical in shape and/or circular in cross-section. Other shapes, cross-sections, and/or configurations are also contemplated.

The method may include heat setting the tubular scaffold 108 on the mandrel. In some embodiments, the method may include heat setting the tubular scaffold 108 on the mandrel in the expanded configuration. In some embodiments, the method may include heat setting the tubular scaffold 108 on a first mandrel in the collapsed configuration at a first temperature such that the tubular scaffold 108 and/or the endoprosthesis 100 is self-biased toward the collapsed configuration at the first temperature, and heat setting the tubular scaffold 108 on a second mandrel in the expanded configuration at a second temperature different from the first temperature such that the tubular scaffold 108 and/or the endoprosthesis 100 is self-biased toward the expanded configuration at the second temperature. Other configurations are also contemplated.

The method may include, after the heat setting step, removing the medial portion of the first row of loops of the plurality of rows of loops 120 and medial portions of rows of rungs immediately adjacent to the first row of loops along a majority of the length of the tubular scaffold 108 to form the first cutout region 160. In some embodiments, the method may include, after the heat setting step, removing the medial portion of the second row of loops of the plurality of rows of loops 120 and medial portions of rows of rungs immediately adjacent to the second row of loops along a majority of the length of the tubular scaffold 108 to form the second cutout region 180. As discussed herein, the second cutout region 180 may be circumferentially spaced apart from the first cutout region 160.

The method may include, after the removing step(s), applying the polymeric covering 150 to the tubular scaffold 108, wherein the polymeric covering 150 is uninterrupted along and/or within the first cutout region 160 and/or the second cutout region 180. In some embodiments, the polymeric covering 150 may be applied via spray coating, dip coating, shrink wrap, and/or other suitable methods. In some embodiments, the polymeric covering 150 may be formed from silicone. In some embodiments, a thickness of the polymeric covering 150 may vary along the length of the endoprosthesis 100 and/or the tubular scaffold 108. In one example, the thickness of the polymeric covering 150 may be increased along and/or within the first cutout region 160 and/or the second cutout region 180 compared to a remainder of the endoprosthesis 100 and/or the tubular scaffold 108. In another example, the thickness of the polymeric covering 150 may be increased along the first plurality of terminal ends 168 and/or the second plurality of terminal ends 188. Other configurations and/or materials are also contemplated.

In some embodiments, prior to applying the polymeric covering 150 to the tubular scaffold 108, the method may include securing and/or fixedly attaching the first plurality of terminal ends 168 and/or the second plurality of terminal ends 188 to an immediately adjacent row of loops of the plurality of rows of loops 120. In some embodiments, the first plurality of terminal ends 168 and/or the second plurality of terminal ends 188 may be welded (e.g., laser welded, sonic welded, etc.) to an immediately adjacent row of loops of the plurality of rows of loops 120. Other configurations are also contemplated.

Figure 11:
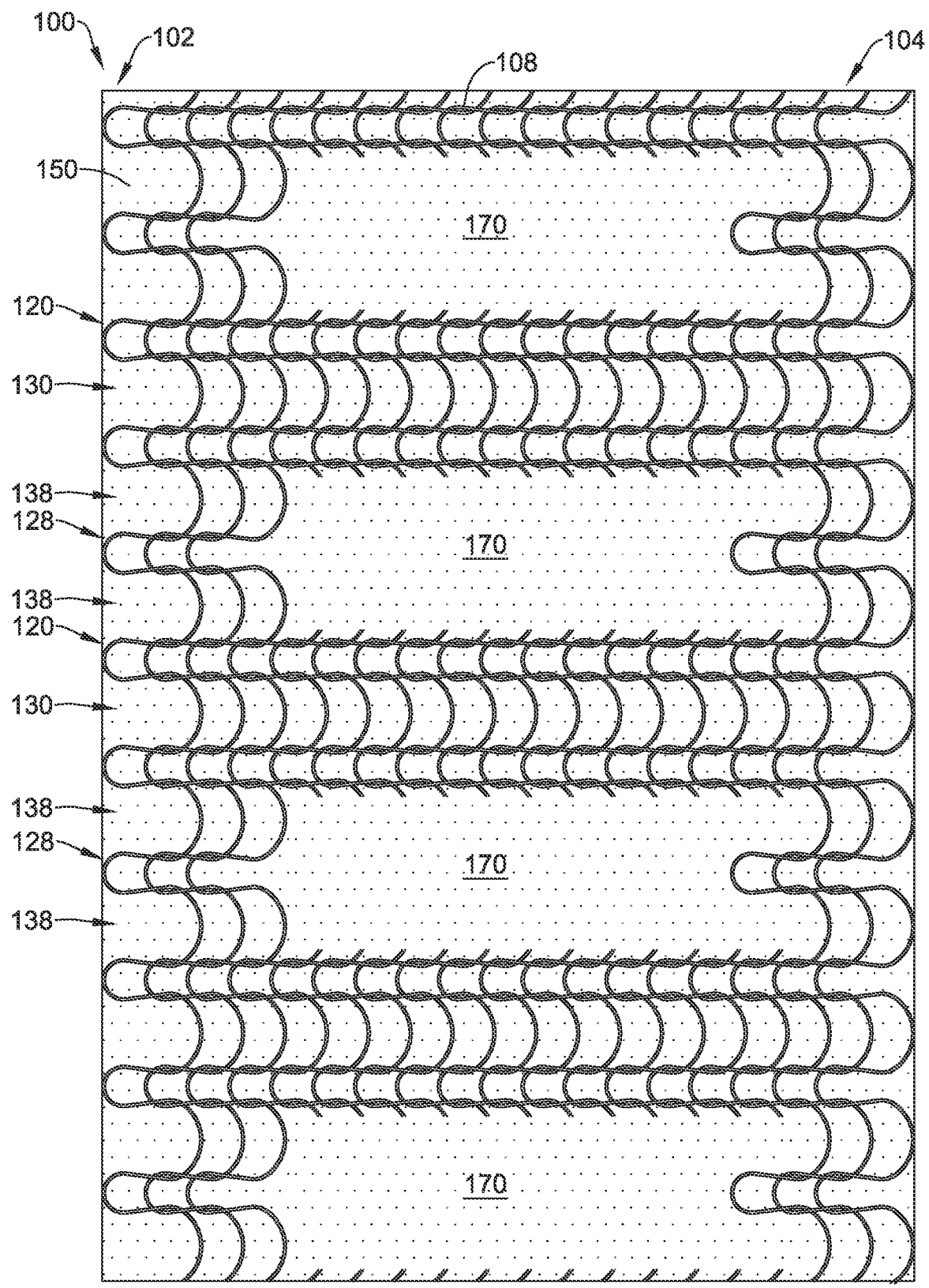
FIG. 11 illustrates an alternative configuration of an endoprosthesis according to the disclosure.

FIG. 11 illustrates an alternative configuration of the endoprosthesis 100. The endoprosthesis 100 may be constructed substantially as described above, with changes noted below. In some embodiments, the endoprosthesis 100 and/or the tubular scaffold 108 may include a plurality of cutout regions 170 extending along a majority of the length of the tubular scaffold 108. In some embodiments, the plurality of cutout regions 170 may include two cutout regions, three cutout regions, four cutout regions, five cutout regions, etc.

In some embodiments, the plurality of cutout regions 170 may extend along at least 60% of the length of the tubular scaffold 108. In some embodiments, the plurality of cutout regions 170 may extend along at least 70% of the length of the tubular scaffold 108. In some embodiments, the plurality of cutout regions 170 may extend along at least 75% of the length of the tubular scaffold 108. In some embodiments, the plurality of cutout regions 170 may extend along at least 80% of the length of the tubular scaffold 108. In some embodiments, the plurality of cutout regions 170 may extend along at least 85% of the length of the tubular scaffold 108. In some embodiments, the plurality of cutout regions 170 may extend along at least 90% of the length of the tubular scaffold 108. Other configurations are also contemplated.

The plurality of cutout regions 170 may be disposed between the proximal end 102 of the tubular scaffold 108 and the distal end 104 of the tubular scaffold 108. The plurality of cutout regions 170 may each define a proximal end oriented toward the proximal end 102 of the tubular scaffold 108 and a distal end oriented toward the distal end 104 of the tubular scaffold 108. In some embodiments, the proximal end of the plurality of cutout regions 170 may be disposed distal of the proximal end 102 of the tubular scaffold 108. In some embodiments, the distal end of the plurality of cutout regions 170 may be disposed proximal of the distal end 104 of the tubular scaffold 108.

In some embodiments, the plurality of cutout regions 170 may each be formed by removing a medial portion of one row of loops 128 of the plurality of rows of loops 120 and medial portions of rows of rungs 138 of the plurality of rows of rungs 130 immediately adjacent to the one row of loops 128 along the majority of the length of the tubular scaffold 108. In some embodiments, the one row of loops 128 of the plurality of rows of loops 120 may be discontinuous along a medial region of the tubular scaffold 108 and rows of rungs 138 on opposite sides of the one row of loops 128 in a circumferential direction from the one row of loops 128 are discontinuous along the medial region of the tubular scaffold 108.

The plurality of cutout regions 170 may be formed after heat setting the tubular scaffold 108, the single filament, and/or the plurality of rows of loops 120 and the plurality of rows of rungs 130. In at least some embodiments, forming the plurality of cutout regions 170 may cause the single filament to be discontinuous within the plurality of cutout regions 170 and/or along the length of the tubular scaffold 108. Similarly, forming the plurality of cutout regions 170 may cause the one row of loops 128 and rows of rungs 138 immediately adjacent the one row of loops 128 to be discontinuous within their respective cutout region 170 and/or along the length of the tubular scaffold 108. In some embodiments, within the medial region of the tubular scaffold 108 the single filament may comprise a plurality of discontinuous segments.

The discontinuous single filament may comprise and/or the plurality of discontinuous segments may form a plurality of terminal ends extending along the plurality of cutout regions 170 and/or the medial region. The plurality of terminal ends may be in close proximity to one of the plurality of rows of loops 120 and/or a perimeter of the plurality of cutout regions 170. For example, the plurality of terminal ends 168 may be within about 0.01 millimeters (mm), 0.02 mm, 0.03 mm, 0.05 mm, 0.07 mm, 0.10 mm, 0.15 mm, 0.25 mm, 0.5 mm, 0.75 mm, 1 mm, etc. of one of the plurality of rows of loops 120. Since the tubular scaffold 108, the single filament, and/or the plurality of rows of loops 120 and the plurality of rows of rungs 130 were heat set prior to forming the plurality of cutout regions 170 and/or prior to removing the medial portion of the one row of loops 128 of the plurality of rows of loops 120 and medial portions of rows of rungs 138 of the plurality of rows of rungs 130 immediately adjacent to the one row of loops 128 along the majority of the length of the tubular scaffold 108, the tubular scaffold 108 is prevented from unraveling even when the medial portion(s) is removed and/or the plurality of cutout regions 170 is formed.

In some embodiments, the plurality of cutout regions 170 may be circumferentially spaced apart from each other. In some embodiments, the plurality of cutout regions 170 may be equally circumferentially spaced apart around the circumference of the tubular scaffold 108 and/or the endoprosthesis 100. In some embodiments, the plurality of cutout regions 170 may be unequally circumferentially spaced apart around the circumference of the tubular scaffold 108 and/or the endoprosthesis 100. The endoprosthesis 100 may include the polymeric covering 150 as described herein.

In some embodiments, the polymeric covering 150 may be uninterrupted along and/or within the plurality of cutout regions 170. In some embodiments, the polymeric covering 150 may be uninterrupted along and/or within at least some of the plurality of cutout regions 170. In some embodiments, the polymeric covering 150 may be uninterrupted along and/or within each and/or all of the plurality of cutout regions 170. In some embodiments, the plurality of terminal ends may be embedded within the polymeric covering 150. In some embodiments, the polymeric covering 150 may be continuous along the medial region of the tubular scaffold 108.

In an alternative configuration, the plurality of cutout regions 170 may each be formed by removing a medial portion of only one row of rungs of the plurality of rows of rungs 130 along the majority of the length of the tubular scaffold 108. In some embodiments, the plurality of cutout regions 170 may be formed without removing any portion(s) of the plurality of rows of loops 120. As such, the plurality of rows of loops 120 may each be continuous from the proximal end 102 to the distal end 104 and each row of rungs having a cutout region formed therein may be discontinuous between the proximal end 102 and the distal end 104. Other configurations are also contemplated.

Figure 12:
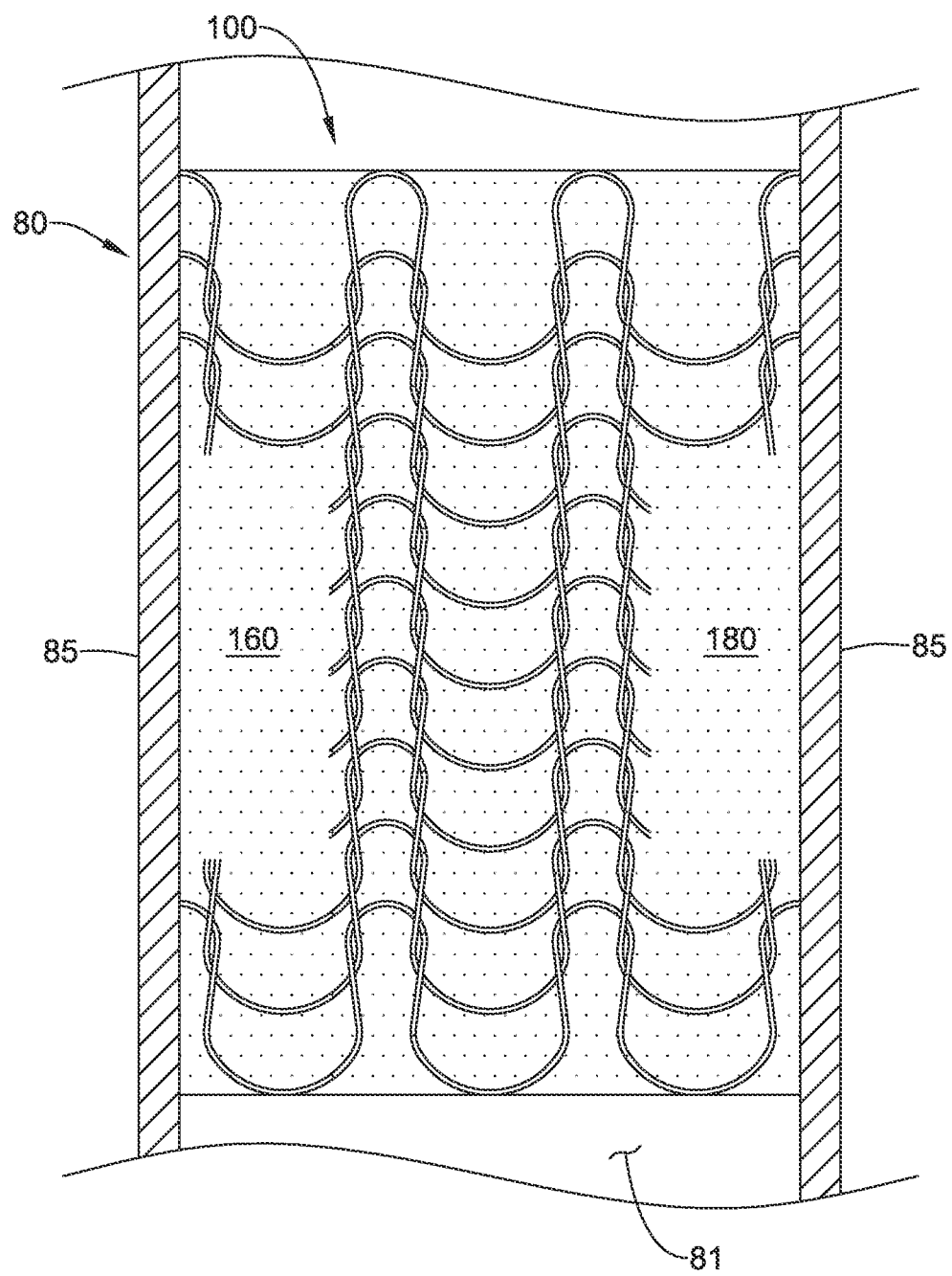
FIG. 12 illustrates an exemplary placement of an endoprosthesis of the disclosure within a trachea.

FIG. 12 illustrates an example placement of the endoprosthesis 100 within the trachea 80. In some embodiments, the first cutout region 160 and/or the second cutout region 180 may be disposed and/or arranged along the lateral walls 85 of the trachea 80. In this position, as the trachea 80 and/or the lumen 81 thereof is deformed by the trachealis muscle 88 (not shown) during forced inspiration/expiration and/or coughing, the endoprosthesis 100 may deflect and/or deform sufficiently to mitigate the high stresses formed at the corner spines 22 of the prior art knitted stent 10 (e.g., FIG. 3), thereby reducing the effects of fatigue and increasing the longevity of the endoprosthesis 100.

The materials that can be used for the various components of the endoprosthesis 100 and the various elements thereof disclosed herein may include those commonly associated with medical devices. For simplicity purposes, the following discussion makes reference to the endoprosthesis. However, this is not intended to limit the devices and methods described herein, as the discussion may be applied to other elements, members, components, or devices disclosed herein, such as, but not limited to, the tubular scaffold, the polymeric cover, and/or elements or components thereof.

In some embodiments, the endoprosthesis and/or components thereof may be made from a metal, metal alloy, polymer (some examples of which are disclosed below), a metal-polymer composite, ceramics, combinations thereof, and the like, or other suitable material.

Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), MARLEX® high-density polyethylene, MARLEX® low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro (propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, polyurethane silicone copolymers (for example, ElastEon® from Aortech Biomaterials or ChronoSil® from AdvanSource Biomaterials), biocompatible polymers, other suitable materials, or mixtures, combinations, copolymers thereof, polymer/metal composites, and the like. In some embodiments the sheath can be blended with a liquid crystal polymer (LCP). For example, the mixture can contain up to about 6 percent LCP.

Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys;

cobalt-chromium-molybdenum alloys (e.g., UNS: R30003 such as ELGILOY®, PHYNOX®, and the like); platinum enriched stainless steel; titanium; platinum; palladium; gold; combinations thereof; or any other suitable material.

In some embodiments, a linear elastic and/or non-superelastic nickel-titanium alloy may be in the range of about 50 to about 60 weight percent nickel, with the remainder being essentially titanium. In some embodiments, the composition is in the range of about 54 to about 57 weight percent nickel. One example of a suitable nickel-titanium alloy is FHP-NT alloy commercially available from Furukawa Techno Material Co. of Kanagawa, Japan. Other suitable materials may include ULTANIUM™ (available from Neo-Metrics) and GUM METAL™ (available from Toyota). In some other embodiments, a superelastic alloy, for example a superelastic nitinol can be used to achieve desired properties.

In at least some embodiments, portions or all of the endoprosthesis and/or components thereof may also be doped with, made of, or otherwise include a radiopaque material. Radiopaque materials are understood to be materials capable of producing a relatively bright image on a fluoroscopy screen or another imaging technique during a medical procedure. This relatively bright image aids the user of the endoprosthesis in determining its location. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of the endoprosthesis to achieve the same result.

In some embodiments, a degree of Magnetic Resonance Imaging (MM) compatibility is imparted into the endoprosthesis and/or other elements disclosed herein. For example, the endoprosthesis and/or components or portions thereof may be made of a material that does not substantially distort the image and create substantial artifacts (i.e., gaps in the image). Certain ferromagnetic materials, for example, may not be suitable because they may create artifacts in an MM image. The endoprosthesis or portions thereof may also be made from a material that the Mill machine can image. Some materials that exhibit these characteristics include, for example, tungsten, cobalt-chromium-molybdenum alloys (e.g., UNS: R30003 such as ELGILOY®, PHYNOX®, and the like), nickel-cobalt-chromium-molybdenum alloys (e.g., UNS: R30035 such as MP35-N® and the like), nitinol, and the like, and others.

In some embodiments, the endoprosthesis and/or other elements disclosed herein may include a fabric material disposed over or within the structure. The fabric material may be composed of a biocompatible material, such a polymeric material or biomaterial, adapted to promote tissue ingrowth. In some embodiments, the fabric material may include a bioabsorbable material. Some examples of suitable fabric materials include, but are not limited to, polyethylene glycol (PEG), nylon, polytetrafluoroethylene (PTFE, ePTFE), a polyolefinic material such as a polyethylene, a polypropylene, polyester, polyurethane, and/or blends or combinations thereof.

In some embodiments, the endoprosthesis and/or other elements disclosed herein may include and/or be formed from a textile material. Some examples of suitable textile materials may include synthetic yarns that may be flat, shaped, twisted, textured, pre-shrunk or un-shrunk. Synthetic biocompatible yarns suitable for use in the present disclosure include, but are not limited to, polyesters, including polyethylene terephthalate (PET) polyesters, polypropylenes, polyethylenes, polyurethanes, polyolefins, polyvinyls, polymethylacetates, polyamides, naphthalene dicarboxylene derivatives, natural silk, and polytetrafluoroethylenes. Moreover, at least one of the synthetic yarns may be a metallic yarn or a glass or ceramic yarn or fiber. Useful metallic yarns include those yarns made from or containing stainless steel, platinum, gold, titanium, tantalum, or a Ni—Co—Cr-based alloy. The yarns may further include carbon, glass, or ceramic fibers. Desirably, the yarns are made from thermoplastic materials including, but not limited to, polyesters, polypropylenes, polyethylenes, polyurethanes, polynaphthalenes, polytetrafluoroethylenes, and the like. The yarns may be of the multifilament, monofilament, or spun-types. The type and denier of the yarn chosen may be selected in a manner which forms a biocompatible and implantable prosthesis and, more particularly, a vascular structure having desirable properties.

In some embodiments, the endoprosthesis and/or other elements disclosed herein may include and/or be treated with a suitable therapeutic agent. Some examples of suitable therapeutic agents may include anti-thrombogenic agents (such as heparin, heparin derivatives, urokinase, and PPack (dextrophenylalanine proline arginine chloromethylketone)); anti-proliferative agents (such as enoxaparin, angiopeptin, monoclonal antibodies capable of blocking smooth muscle cell proliferation, hirudin, and acetylsalicylic acid); anti-inflammatory agents (such as dexamethasone, prednisolone, corticosterone, budesonide, estrogen, sulfasalazine, and mesalamine); antineoplastic/antiproliferative/anti-mitotic agents (such as paclitaxel, 5-fluorouracil, cisplatin, vinblastine, vincristine, epothilones, endostatin, angiostatin and thymidine kinase inhibitors); anesthetic agents (such as lidocaine, bupivacaine, and ropivacaine); anti-coagulants (such as D-Phe-Pro-Arg chloromethyl keton, an RGD peptide-containing compound, heparin, anti-thrombin compounds, platelet receptor antagonists, anti-thrombin antibodies, anti-platelet receptor antibodies, aspirin, prostaglandin inhibitors, platelet inhibitors, and tick antiplatelet peptides); vascular cell growth promoters (such as growth factor inhibitors, growth factor receptor antagonists, transcriptional activators, and translational promoters); vascular cell growth inhibitors (such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin); cholesterol-lowering agents; vasodilating agents; and agents which interfere with endogenous vasoactive mechanisms.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The disclosure's scope is, of course, defined in the language in which the appended claims are expressed.

What is claimed is:

1. An endoprosthesis configured to shift between a collapsed configuration and an expanded configuration, the endoprosthesis comprising:
   a tubular scaffold formed from a single filament knitted about a central longitudinal axis and defining a length from a proximal end to a distal end, the tubular scaffold including a plurality of rows of loops and a plurality of rows of rungs arranged around the central longitudinal axis in an alternating fashion; and a polymeric covering extending along the tubular scaffold;

wherein each row of loops extends longitudinally along the tubular scaffold between the proximal end and the distal end;

wherein each row of rungs extends longitudinally along the tubular scaffold between the proximal end and the distal end;

wherein the tubular scaffold includes:
- a first cutout region extending along a majority of the length of the tubular scaffold and defining a first proximal end oriented toward the proximal end of the tubular scaffold and a first distal end oriented toward the distal end of the tubular scaffold; and
- a second cutout region extending along a majority of the length of the tubular scaffold and defining a second proximal end oriented toward the proximal end of the tubular scaffold and a second distal end oriented toward the distal end of the tubular scaffold;

wherein the polymeric covering is uninterrupted along the first cutout region and the second cutout region; and wherein the first cutout region is formed by removing a medial portion of a first row of loops and medial portions of rows of rungs immediately adjacent to the first row of loops along the majority of the length of the tubular scaffold.

2. The endoprosthesis of claim 1, wherein forming the first cutout region causes the single filament to be discontinuous within the first cutout region.

3. The endoprosthesis of claim 2, wherein the discontinuous single filament comprises a first plurality of terminal ends extending along the first cutout region.

4. The endoprosthesis of claim 1, wherein the second cutout region is formed by removing a medial portion of a second row of loops and medial portions of rows of rungs immediately adjacent to the second row of loops along the majority of the length of the tubular scaffold.

5. The endoprosthesis of claim 4, wherein forming the second cutout region causes the single filament to be discontinuous within the second cutout region.

6. The endoprosthesis of claim 5, wherein the discontinuous single filament comprises a second plurality of terminal ends extending along the second cutout region.

7. The endoprosthesis of claim 1, wherein the second cutout region is circumferentially spaced apart from the first cutout region.

8. The endoprosthesis of claim 1, wherein the first proximal end and the second proximal end are disposed distal of the proximal end of the tubular scaffold;

wherein the first distal end and the second distal end are disposed proximal of the distal end of the tubular scaffold.

9. The endoprosthesis of claim 1, wherein the first cutout region extends along at least 60% of the length of the tubular scaffold.

10. The endoprosthesis of claim 1, wherein the first cutout region extends along at least 75% of the length of the tubular scaffold.

11. An endoprosthesis configured to shift between a collapsed configuration and an expanded configuration, the endoprosthesis comprising:
- a tubular scaffold formed from a single filament knitted about a central longitudinal axis and defining a length from a proximal end to a distal end, the tubular scaffold including a plurality of rows of loops and a plurality of rows of rungs arranged around the central longitudinal axis in an alternating fashion; and
- a polymeric covering extending along the tubular scaffold;

wherein each row of loops extends longitudinally along the tubular scaffold between the proximal end and the distal end;

wherein each row of rungs extends longitudinally along the tubular scaffold between the proximal end and the distal end;

wherein a first row of loops of the plurality of rows of loops is discontinuous along a medial region of the tubular scaffold and rows of rungs on circumferentially opposite sides of the first row of loops are discontinuous along the medial region of the tubular scaffold;

wherein a second row of loops of the plurality of rows of loops circumferentially opposite the first row of loops is discontinuous along the medial region of the tubular scaffold and rows of rungs on opposite sides of the second row of loops are discontinuous along the medial region of the tubular scaffold;

wherein the polymeric covering is continuous along the medial region of the tubular scaffold;

wherein the polymeric covering is formed from silicone;

where the medial region extends along at least 60% of the length of the tubular scaffold.

12. The endoprosthesis of claim 11, wherein within the medial region the single filament comprises a plurality of discontinuous segments.

13. The endoprosthesis of claim 12, wherein the plurality of discontinuous segments forms a plurality of terminal ends along the medial region, the plurality of terminal ends being embedded within the polymeric covering.

14. The endoprosthesis of claim 11, wherein the endoprosthesis is self-biased toward the expanded configuration.

* * * * *